United States Patent
Carlson et al.

(10) Patent No.: US 9,036,881 B2
(45) Date of Patent: May 19, 2015

(54) REDUCTION AND REMOVAL OF ARTIFACTS FROM A THREE-DIMENSIONAL DENTAL X-RAY DATA SET USING SURFACE SCAN INFORMATION

(75) Inventors: Bradley S. Carlson, Huntington, NY (US); Edward Marandola, Gwynedd, PA (US); David A. Sebok, Eagleville, PA (US); Uwe Mundry, Landrum, SC (US)

(73) Assignee: DENTAL IMAGING TECHNOLOGIES CORPORATION, Hatfield, PA (US)

(*) Notice: Subject to any disclaimer, the term of this patent is extended or adjusted under 35 U.S.C. 154(b) by 644 days.

(21) Appl. No.: 13/090,786

(22) Filed: Apr. 20, 2011

(65) Prior Publication Data

US 2011/0255765 A1    Oct. 20, 2011

Related U.S. Application Data

(60) Provisional application No. 61/326,031, filed on Apr. 20, 2010.

(51) Int. Cl.
*G06K 9/00* (2006.01)
*A61B 6/03* (2006.01)
(Continued)

(52) U.S. Cl.
CPC ............... *A61B 6/032* (2013.01); *A61B 5/0064* (2013.01); *A61B 6/14* (2013.01); *A61B 6/4085* (2013.01);
(Continued)

(58) Field of Classification Search
CPC .................. G06T 11/005; G06T 2207/30036; A61B 5/0088; A61C 9/004; A61C 9/0053
USPC ................. 382/131, 128, 275; 378/4, 38, 168
See application file for complete search history.

(56) References Cited

U.S. PATENT DOCUMENTS 4,941,164 A * 7/1990 Schuller et al. ............... 378/205
6,068,482 A   5/2000 Snow
(Continued)

FOREIGN PATENT DOCUMENTS

JP    2009-233294    10/2009
JP    2010-068832    4/2010
(Continued)

OTHER PUBLICATIONS

Watzke et al., A Pragmatic approach to metal artifact reduction in CT: merging of metal artifact reduced images [on-line], May 2004 [retrieved Jan. 6, 2015], European Radiology, vol. 14, Issue 5, pp. 849-856. Retrieved from the Internet: http://link.springer.com/article/10.1007/s00330-004-2263-y.*

(Continued)

*Primary Examiner* — Matthew Bella
*Assistant Examiner* — Dennis Rosario
(74) *Attorney, Agent, or Firm* — Michael Best & Friedrich LLP

(57) ABSTRACT

A system for removing artifacts caused by x-ray reflective materials from an x-ray image of a patient's teeth. The system includes an x-ray source, an x-ray detector that captures several x-ray images, and a surface scanner that captures a surface scan of the patient's teeth. An image processor generates three-dimensional models from the optical surface data and the CT volumetric data. The models are resized and oriented to be of the same scale and orientation and then overlaid to create a combined data set. Data points that extend beyond the surface of the patient's teeth in the surface model are identified and may be removed if it is determined that they are artifacts. An artifact-reduced CT model is then displayed.

12 Claims, 10 Drawing Sheets

(51) Int. Cl.
*A61B 5/00* (2006.01)
*A61B 6/14* (2006.01)
*A61B 6/00* (2006.01)
*G06T 5/00* (2006.01)
*G06T 11/00* (2006.01)

(52) U.S. Cl.
CPC .............. *A61B 6/4435* (2013.01); *A61B 6/5247* (2013.01); *A61B 6/5258* (2013.01); *G06T 5/005* (2013.01); *G06T 2207/10081* (2013.01); *G06T 2207/30036* (2013.01); *G06T 11/008* (2013.01)

(56) References Cited

U.S. PATENT DOCUMENTS

| | | | |
|---|---|---|---|
| 6,152,731 A * | 11/2000 | Jordan et al. | 433/69 |
| 6,671,529 B2 | 12/2003 | Claure et al. | |
| 6,845,175 B2 | 1/2005 | Kopelman et al. | |
| 7,200,642 B2 | 4/2007 | Hultgren et al. | |
| 7,574,025 B2 | 8/2009 | Feldman | |
| 7,991,243 B2 * | 8/2011 | Bal et al. | 382/275 |
| 8,170,327 B2 * | 5/2012 | Glor et al. | 382/154 |
| 8,199,988 B2 * | 6/2012 | Marshall et al. | 382/128 |
| 8,364,301 B2 * | 1/2013 | Schmitt | 700/118 |
| 2004/0197727 A1 | 10/2004 | Sachdeva et al. | |
| 2007/0190481 A1 | 8/2007 | Schmitt | |
| 2008/0228303 A1 * | 9/2008 | Schmitt | 700/98 |
| 2009/0220916 A1 | 9/2009 | Fisker et al. | |
| 2009/0238334 A1 | 9/2009 | Brahme et al. | |
| 2009/0295795 A1 | 12/2009 | Feldman | |
| 2009/0316966 A1 | 12/2009 | Marshall et al. | |
| 2010/0124367 A1 | 5/2010 | Cizek | |

FOREIGN PATENT DOCUMENTS

| | | |
|---|---|---|
| WO | 2004098379 | 11/2004 |
| WO | 2008083874 | 7/2008 |

OTHER PUBLICATIONS

Nkenke, E. et al., "Fusion of computed tomography data and optical 3D images of the dentition for streak artefact correction in the simulation of orthognatic surgery," Dentomaxillofacial Radiology (2004) 33:226-232.

First Office Action from The State Intellectual Property Office of the People's Republic of China for Application No. 201180020294.9 dated Aug. 1, 2014 (22 pages).

English Translation of Second Notice of Preliminary Rejection from the Korean Intellectual Property Office for Application No. 10-2012-7030194 dated Aug. 29, 2014 (4 pages).

\* cited by examiner

REDUCTION AND REMOVAL OF ARTIFACTS FROM A THREE-DIMENSIONAL DENTAL X-RAY DATA SET USING SURFACE SCAN INFORMATION

RELATED APPLICATIONS

This patent application claims priority to U.S. Provisional Patent Application No. 61/326,031 filed on Apr. 20, 2010, titled "REDUCTION AND REMOVAL OF ARTIFACTS FROM A THREE-DIMENSIONAL DENTAL X-RAY DATA SET USING SURFACE SCAN INFORMATION," the entire contents of which are herein incorporated by reference.

BACKGROUND

The present invention relates to dental imaging technology. More specifically, the present invention relates to reconstructing a three-dimensional image of a patient's teeth using both x-ray and surface scanning technology.

X-ray technology can be used to generate a three-dimensional, digital representation of a subject using computed tomography (CT). However, metal and other objects can reflect x-rays that would otherwise penetrate through human tissue and be detected by the x-ray detector. This reflection can cause unwanted artifacts to appear in the captured data set. This effect is particularly prevalent in dental imaging where foreign substances such as metal fillings or braces are often installed in the patient's mouth.

There are some prior systems in which artifacts are removed from x-ray data by, simply stated, "combining" x-ray and non-x-ray data. However, as best known by the inventors, in addition to removing or reducing artifacts, such systems also remove significant amounts of desired image data.

U.S. Publication No. 2010/0124367 has suggested that artifacts can be removed from x-ray data by the "fusion of the x-ray data set with an optical image of the jaw, which is completely free of metal artifacts . . . ." However, details regarding how the artifacts would be removed are not provided and the "fusion" disclosed in the '367 publication uses a pre-positioning technique that requires identifying registration points on a screen or other manual means prior to combining the data. While this pre-positioning makes the task of combining the two data sets substantially easier than a completely automatic method, the method requires manual intervention. That is, the x-ray technician, dentist, or other dental professional must manually manipulate the images on a screen.

U.S. Pat. No. 6,671,529 describes a method of creating a composite skull model by combining three-dimensional CT data and laser surface scans of a patient's teeth. In the '529 patent, the teeth are completely removed from the CT model and replaced with only the surface scan data of the patient's teeth.

U.S. Pat. No. 7,574,025 describes a method of removing artifacts from a three-dimensional model (such as CT or MRI) by a negative impression template of the patient's teeth. In the '025 patent, a negative impression template is cast of the patient's teeth. A first model is generated while the negative impression template is placed in the patient's mouth. A second model is generated of only the negative impression template using the same imaging technology as the first. Voxels from the first digital image are substituted for corresponding voxels from the second digital image to create a model of the patient's teeth without artifacts.

SUMMARY

It would be useful to have an improved method and system of removing artifacts from x-ray data that did not remove significant portions of desired CT image data, substitute data from multiple x-rays, or require manual pre-positioning of the data sets.

In one embodiment, the invention provides a system for generating a three-dimensional, digital representation including a patient's teeth using both CT and surface scanning data. The system includes an x-ray source and an x-ray detector that are used to capture several x-ray images. The images are transmitted to an image processing system where they are used to construct a three-dimensional CT model of the patient's teeth. The system also includes a surface scanner (such as a laser or structured light scanning system) that captures data representing the shape and texture of the surface of the patient's teeth. The surface data is also transmitted to the image processing system where it is used to construct a three-dimensional model of the surface of the patient's teeth. The image processing system then resizes and orients the surface model and the CT model so that the two models are of the same scale and orientation.

In some embodiments, the surface model is then overlaid onto the CT model. This is achieved without requiring manual intervention. The system of this embodiment then detects artifacts in the CT model by detecting any data points in the CT model that extend beyond the overlaid surface model. Data points extending beyond the surface model are considered to be artifacts and the image processing system removes the artifact data points from the CT model. In other embodiments, any data points in the CT model that extend beyond the surface model are processed to determine whether they are artifacts. Processed data points that are identified as artifacts are then removed from the CT model. In some embodiments, after the artifact data points are identified and removed from the CT model, the overlaid surface data is then removed leaving only the three-dimensional CT model.

In some embodiments, the surface model is forward projected to create projection data in the same two-dimensional (2D) format as the CT projection data. The forward projected data is combined with the CT projection data to identify regions of metal and teeth and allow the CT reconstruction to remove the effects of metal from the reconstructed CT images. Again, this is achieved without requiring manual pre-positioning of the two sets of data with respect to one another.

Other aspects of the invention will become apparent by consideration of the detailed description and accompanying drawings.

BRIEF DESCRIPTION OF THE DRAWINGS AND APPENDICES

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
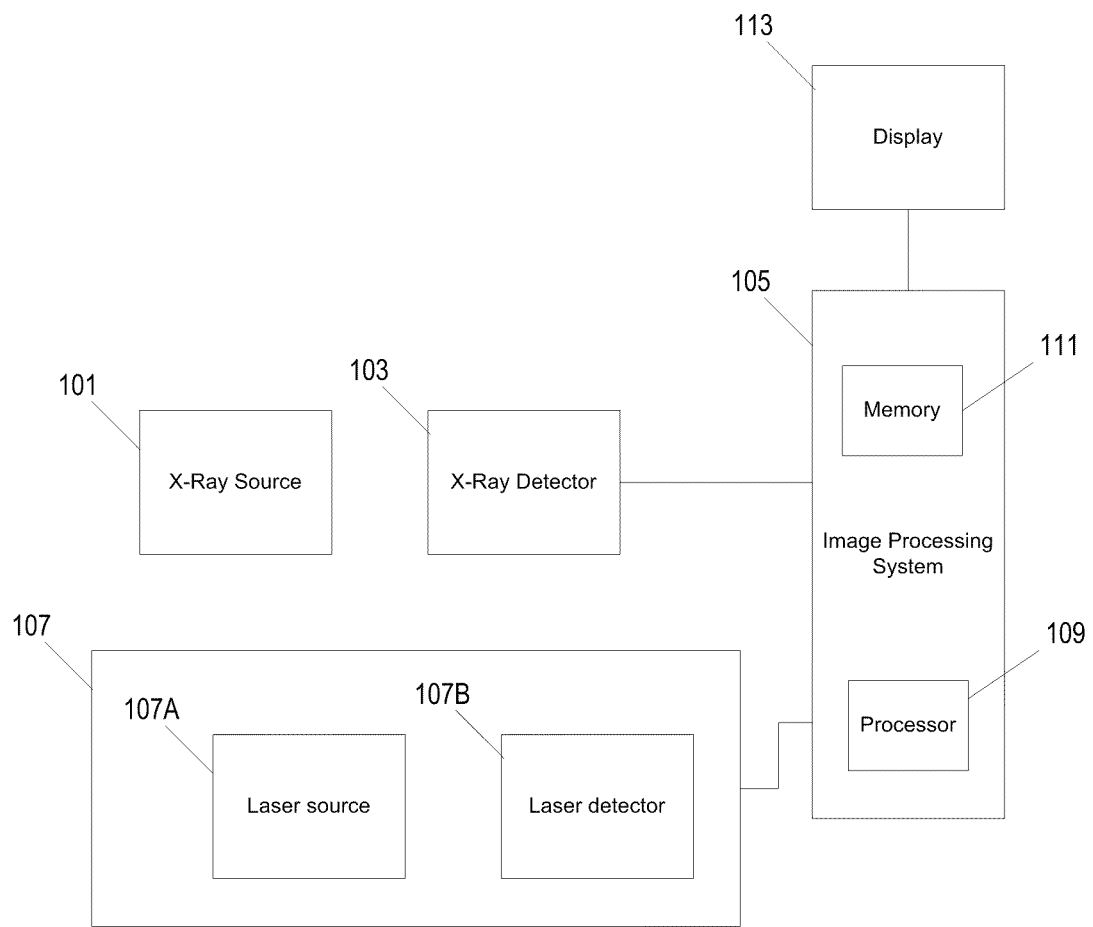
FIG. 1A is a block diagram illustrating the components of the imaging system according to one embodiment of the invention.

FIG. 1A is a block diagram illustrating the components of a system for removing artifacts from a three-dimensional digital CT model of a patient's teeth. The system can also be used to create three-dimensional digital models of the patient's jaw and other facial bones and tissue. The system includes an x-ray source 101 and an x-ray detector 103. The x-ray source 101 is positioned to project x-rays toward a patient's teeth. The x-ray detector 103 is positioned on the opposite side of the patient's teeth—either inside the patient's oral cavity or on the opposite side of the patient's head. The x-rays from the x-ray source 101 are attenuated differently by the patient's tissue and are detected by the x-ray detector 103.

Figure 1B:
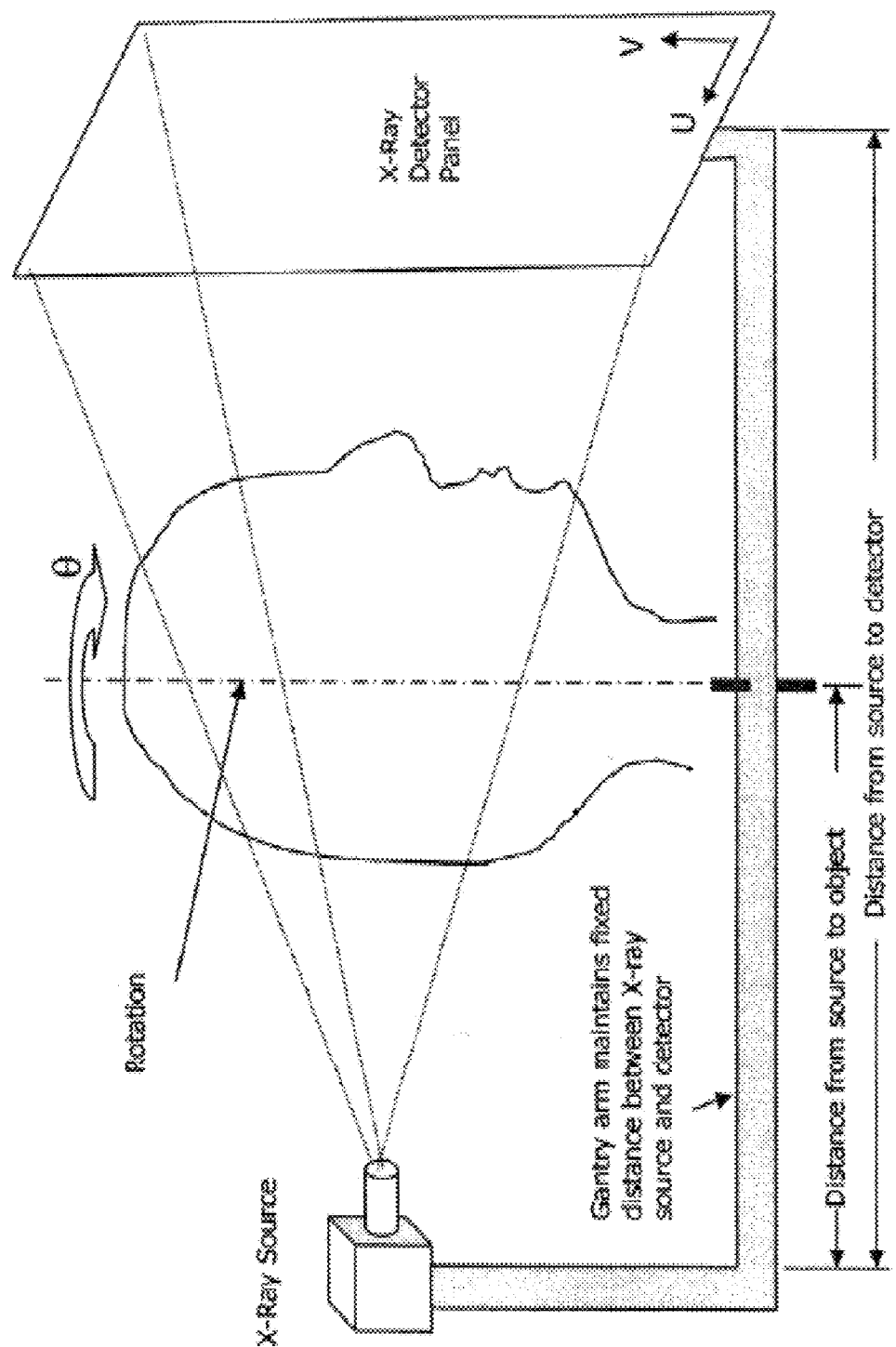
FIG. 1B is a diagram of a cone-beam CT scanning system used in the system of FIG. 1A.

The x-ray detector 103 is connected to an image processing system 105. The data captured by the x-ray detector 103 is used by the image processing system to generate a three-dimensional CT model of the patient's teeth. As such, in one embodiment, the x-ray source 101 and the x-ray detector 103 are part of a cone-beam, scanning CT system that rotates around the patient's head to collect x-ray image data as illustrated in FIG. 1B. An example of one such scanning system is described in U.S. application Ser. No. 12/700,028 filed on Feb. 4, 2010, the entire contents of which are incorporated herein by reference. The '028 application relates to motion correction, but the imaging components—sensor and source mounted on a rotatable C-arm, are applicable to the techniques described herein.

The system illustrated in FIG. 1A also includes a surface scanning imaging system 107. The surface scanning system 107 captures data relating to the surface texture, size, and geometry of the patient's teeth. The captured surface data is then transmitted to the image processing system 105 where it is used to generate a three-dimensional surface model of the patient's teeth. In some embodiments, the surface scanning imaging system includes a laser transceiver system such as one including a laser source 107A and a laser sensor or digital camera 107B. The laser source scans a laser line across the surface of the patient's tooth. The sensor or camera captures images of the projected line. The image processing system 105 analyzes how the shape of the laser line from the perspective of the sensor or camera changes as it is scanned across the patient's tooth. This data is then used to generate the three-dimensional surface model of the patient's teeth.

The image processing system 105 in FIG. 1A includes a processor 109 for executing computer instructions and a memory 111 for storing the instructions and data transmitted from the x-ray detector 103 and the surface scanning system 107. In some embodiments, the image processing system includes one or more desktop computers running image processing software. In other embodiments, the image processing system 105 is a device designed specifically for processing image data received from the x-ray detector 103 and the surface scanning system 107. Data captured by the x-ray detector 103 and the surface scanning imaging system 107 as well as processed volumetric data is displayed on a display 113.

Figure 2:
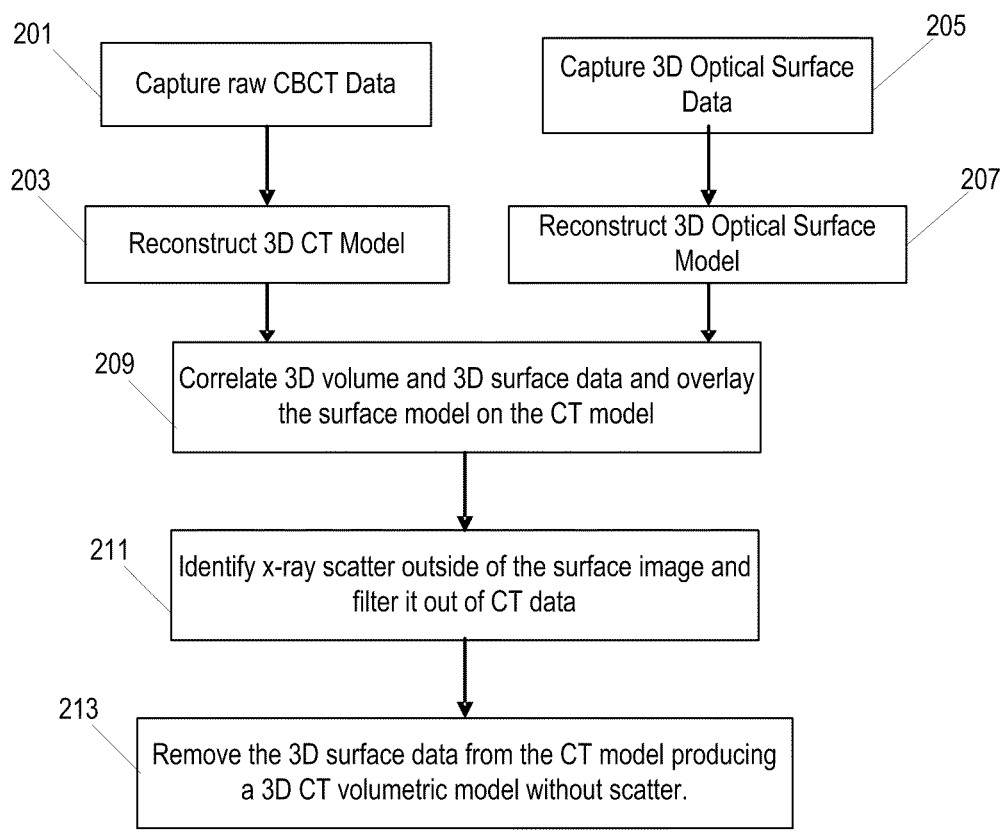
FIG. 2 is a flowchart showing the method of using the system of FIG. 1A to remove artifacts from a CT model.

FIG. 2 is a flowchart illustrating one method for how the system of FIG. 1A can be used to generate to a CT model of a patient's teeth and remove artifacts from a CT model of the patient's teeth. The system begins by capturing cone-beam CT (CBCT) image data of the patient's teeth (step 201). This is done by rotating the x-ray source 101 and the x-ray detector 103 around the patient's head to collect several x-ray images of the patient's teeth. The captured data is then used to generate a three-dimensional CT model of the patient's teeth (step 203). The surface scanning system 107 is used to capture optical surface data (step 205), which the image processing system 105 then uses to generate a three-dimensional surface model of the patient's teeth (step 207). In various embodiments, the surface data can be captured before or after the CT image is captured. Similarly, the CT data can be processed by the image processing system (step 203) before or after the surface data is captured by the surface scanning system 107 (step 205).

After both the CT model and the surface model have been generated, the image processing system 105 correlates the three-dimensional CT volume model and the three-dimensional optical surface model to determines a proper scale and orientation of the two models. The surface model is overlaid onto the CT model to generate a combined data set (step 209). In some embodiments, the system is calibrated such that the captured data includes registration information indicating the location and perspective from which the data was captured. In such embodiments, the proper scale and orientation of the two models is determined by matching the registration information from the CT model to the corresponding registration information from the surface model.

In other embodiments, the image processing system 105 uses surface matching algorithms to identify corresponding physical structures in both of the models. The identification of corresponding structures can be achieved, for example, by the identification of three or more anatomical landmarks that appear in both of the two models and then rotating, translating, and scaling one model until the differences between these landmarks is minimized within a predetermined tolerance. Alternatively, the entire surface in the two models can be matched by scaling, rotation, and translation through various well-known optimization techniques such as simulated annealing. A number of features in the two models can be characterized in each and correlated to determine the best match of the surfaces. The image processing system 105 sizes and orients the models according to the matching structures.

In some embodiments, the overlay process can be executed by overlaying the entire surface model onto the entire CT model. The image processing system 105 can also include various functions that segment the CT model into sub-volumes. The sub-volume functions can be used to isolate a single tooth from the CT model. In FIGS. 5-8, artifacts caused by x-ray reflective materials (such as metal filings) are removed from the CT model by overlaying data from the surface model onto sub-volumes of the CT model one tooth at a time.

Figure 5:
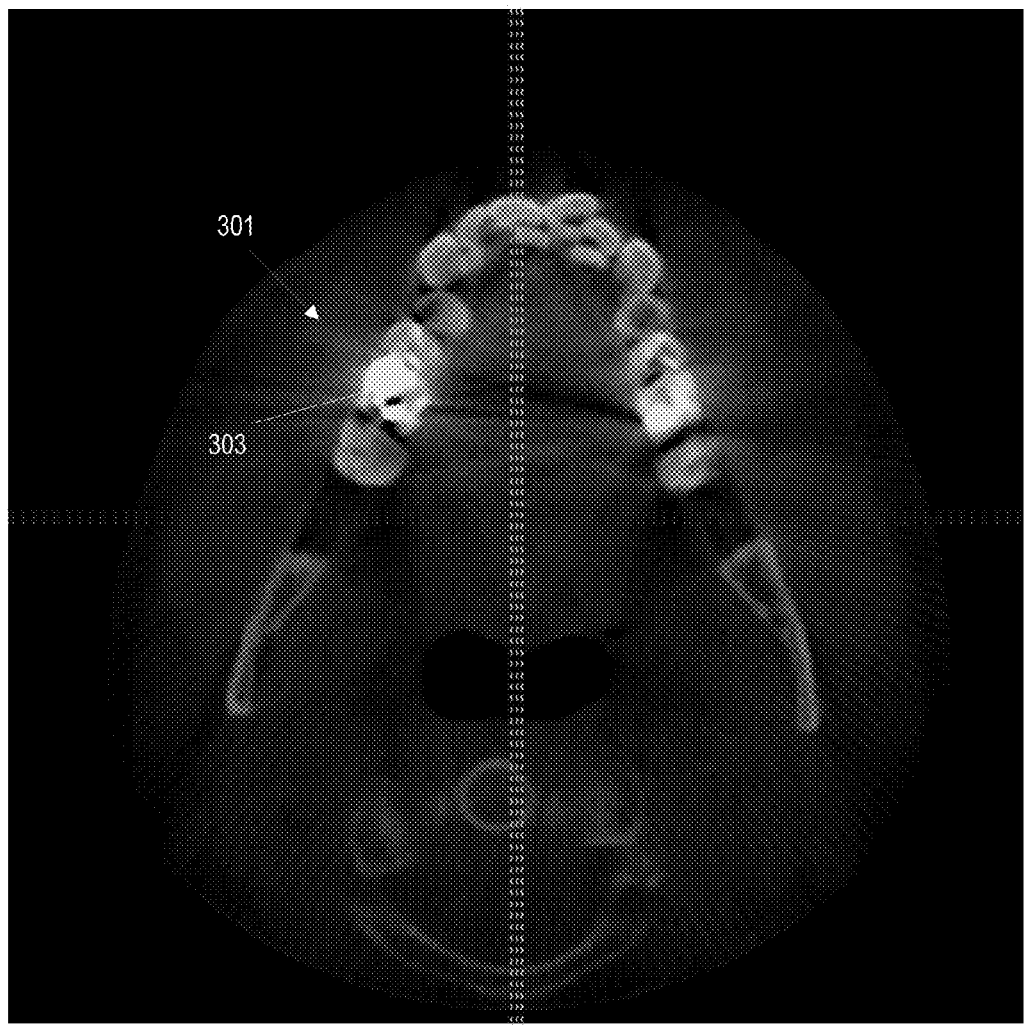
FIG. 5 is an image of a slice of the CT data captured by the x-ray detector of FIG. 1A.
Figure 6:
FIG. 6 is a perspective view of an unfiltered CT model of a patient's teeth and jaw with imaging artifacts.
Figure 7:
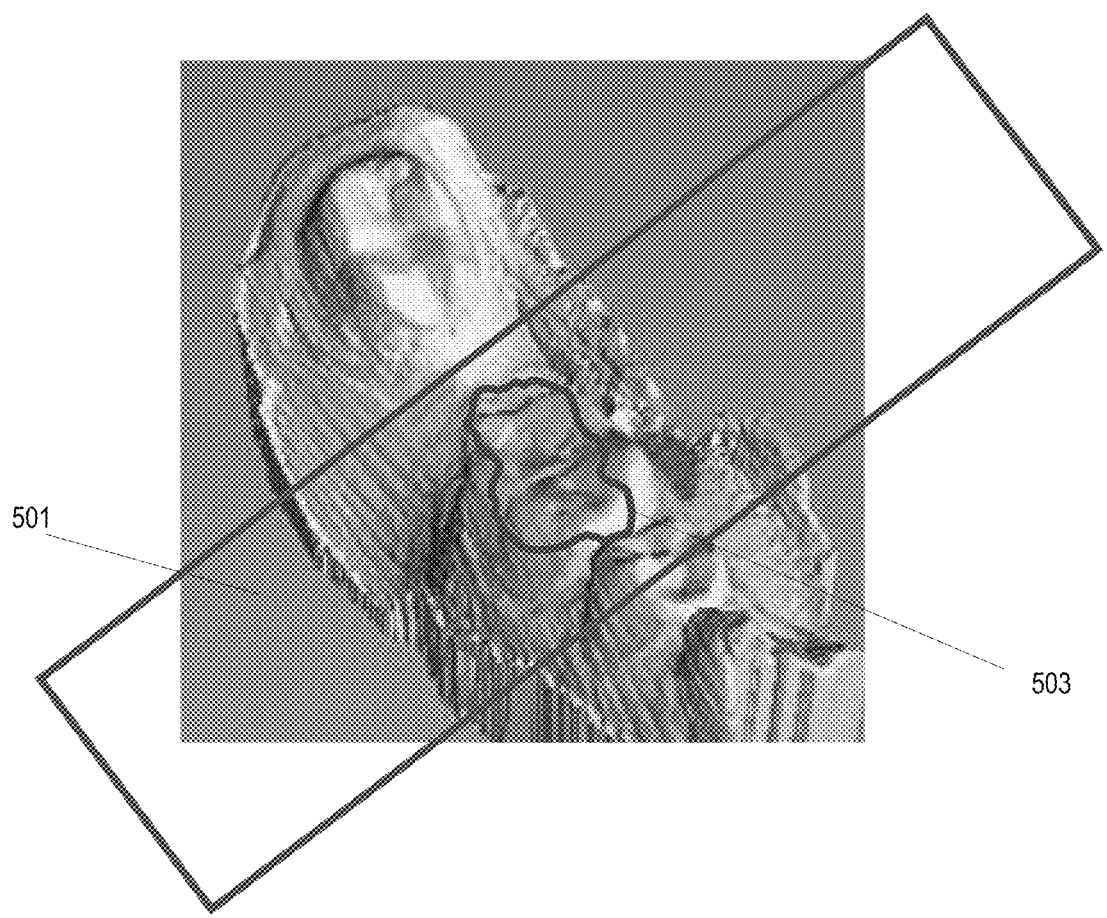
FIG. 7 is an overhead view of a surface model of a patient's teeth captured by the surface scanner of FIG. 1A.
Figure 8:
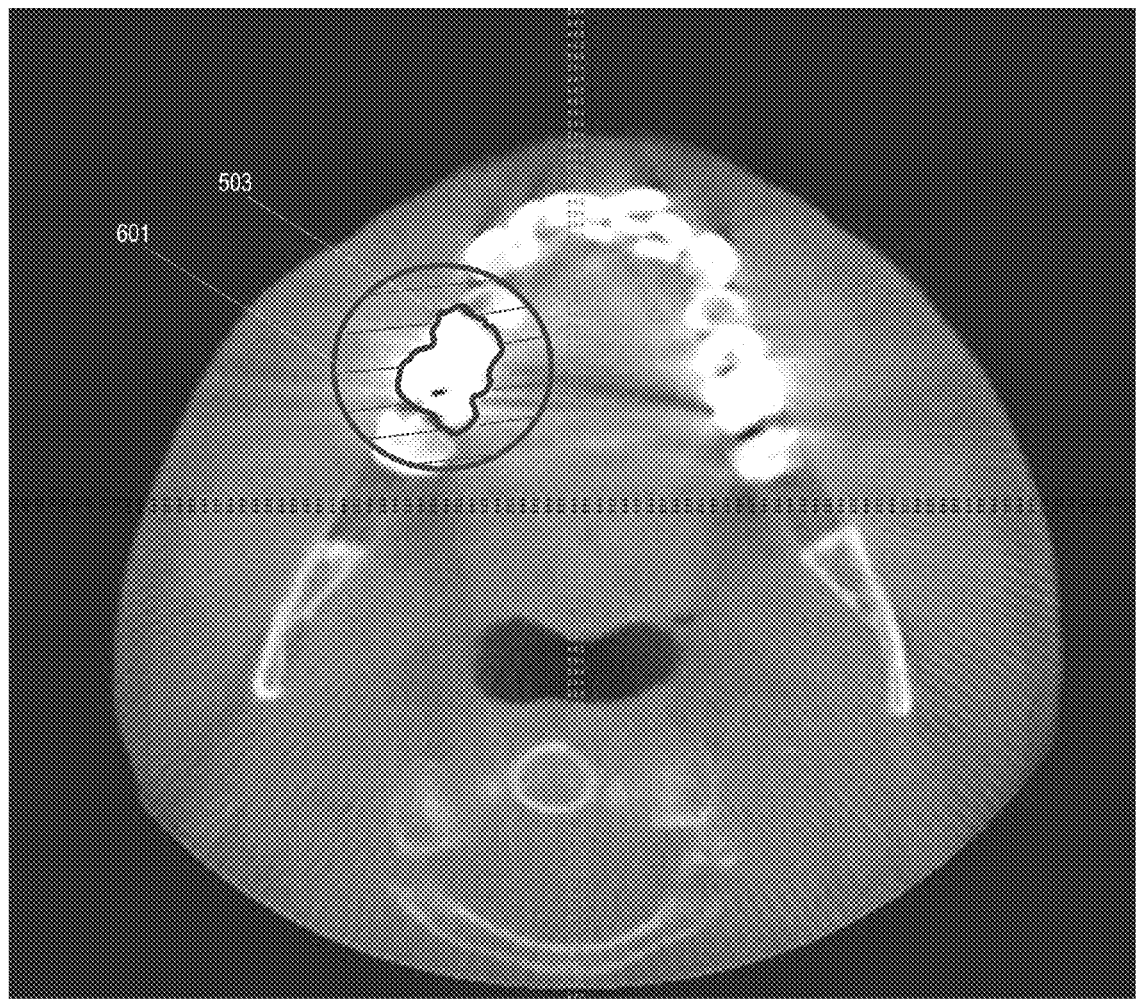
FIG. 8 is an image of a planar silhouette from the surface model of FIG. 5 overlaid onto a slice of the CT data of FIG. 3.

FIG. 5 shows a single horizontal slice from the CT model of the patient's teeth. Artifacts 301 can be seen reflecting from structures in the patient's teeth 303. FIG. 6 shows the fully constructed CT model. Again, artifacts 301 are clearly visible extending from the patient's teeth 303. These artifacts 301 hide some of the surface details of the patient's teeth 303 in the CT model. FIG. 7 shows a portion of the surface model generated by the image processing system 105 based on the surface information captured by the surface scanning system 107. The image processing system isolates a horizontal cut plane 501 in the surface model. This cut plane 501 corresponds to the slice from the CT model illustrated in FIG. 5. Because the surface model does not contain any data points from within the patient's teeth, the cut plane data identifies a silhouette shape 503 that corresponds to the outer surface of the patient's tooth on a given horizontal plane. In FIG. 8, the silhouette shape 503 from the cut plane 501 is overlaid onto the same tooth in the slice from the CT model.

After the silhouette data 503 from the surface model is overlaid onto the corresponding tooth in a slice of the CT model, the image processing system 105 identifies data points in the CT model that extend beyond the silhouette 503 (step 211). If data is detected outside of the silhouette shape 503, the system determines whether this data is artifact data. In some embodiments, all data in the CT model that extends beyond the silhouette shape 503 is assumed to be or is identified as artifact data and is removed from the CT model. In other embodiments, the data outside of the silhouette 503 is processed by a filtering or interpolation algorithm. The interpolation algorithm detects picture elements in the data just outside of the silhouette shape 503 that have densities that are above a threshold. The algorithm then interpolates data for these identified, artifact-associated pixels (or data points) with data from adjacent pixels not associated with artifact. FIG. 8 illustrates an area 601 just outside of the silhouette shape 503 that is to be analyzed by such a filtering algorithm.

After the CT data outside of the silhouette shape 503 has been interpolated, adjusted, or removed, the image processing system 105 moves onto another tooth in the same slice of CT data. After the necessary corrections have been made for each tooth, the image processing system 105 moves to another slice of CT data. This process repeats until all of the teeth in each of the CT data slices have been analyzed and the artifact data has been removed.

Figure 9:
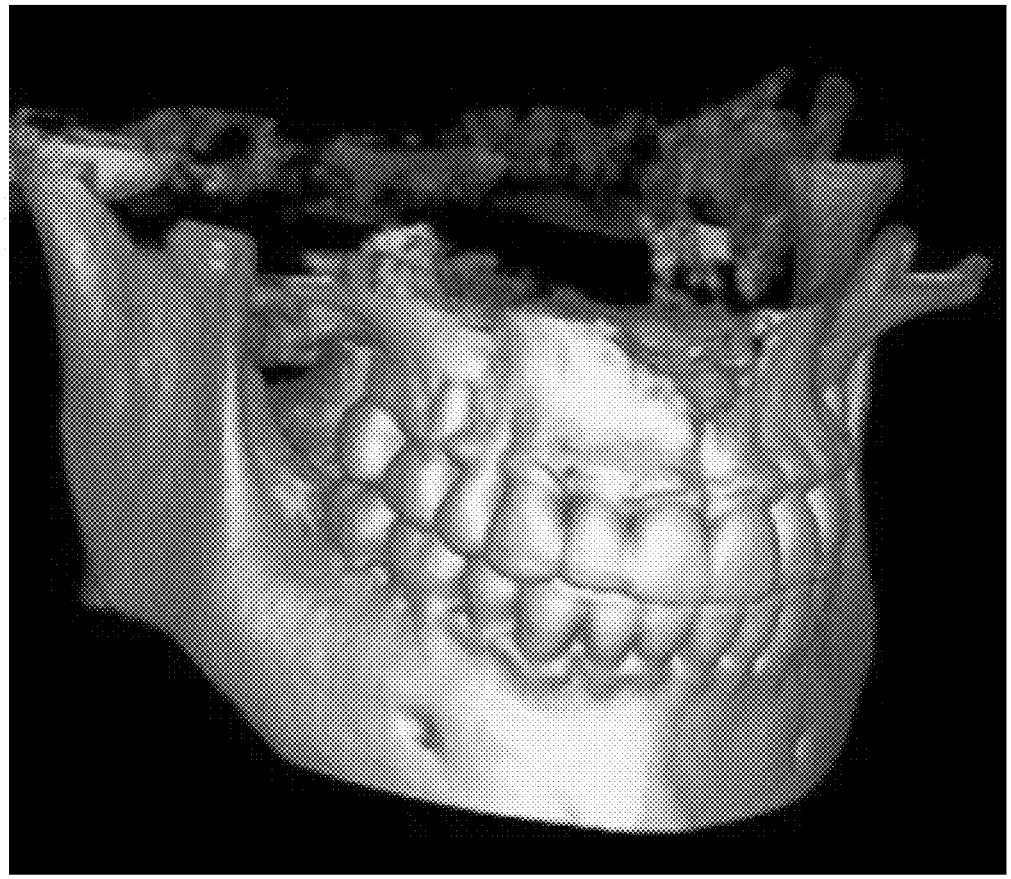
FIG. 9 is a perspective view of the CT model of FIG. 4 with the imaging artifacts removed.

After the CT data has been analyzed and the artifacts have been identified and removed, the image processing system 105 removes the overlaid surface model and any silhouette shapes from the CT data (step 213) and generates an artifact-reduced CT model. As pictured in FIG. 9, the artifacts have been removed from the artifact-reduced CT model and the surface of each tooth is visible.

Figure 3:
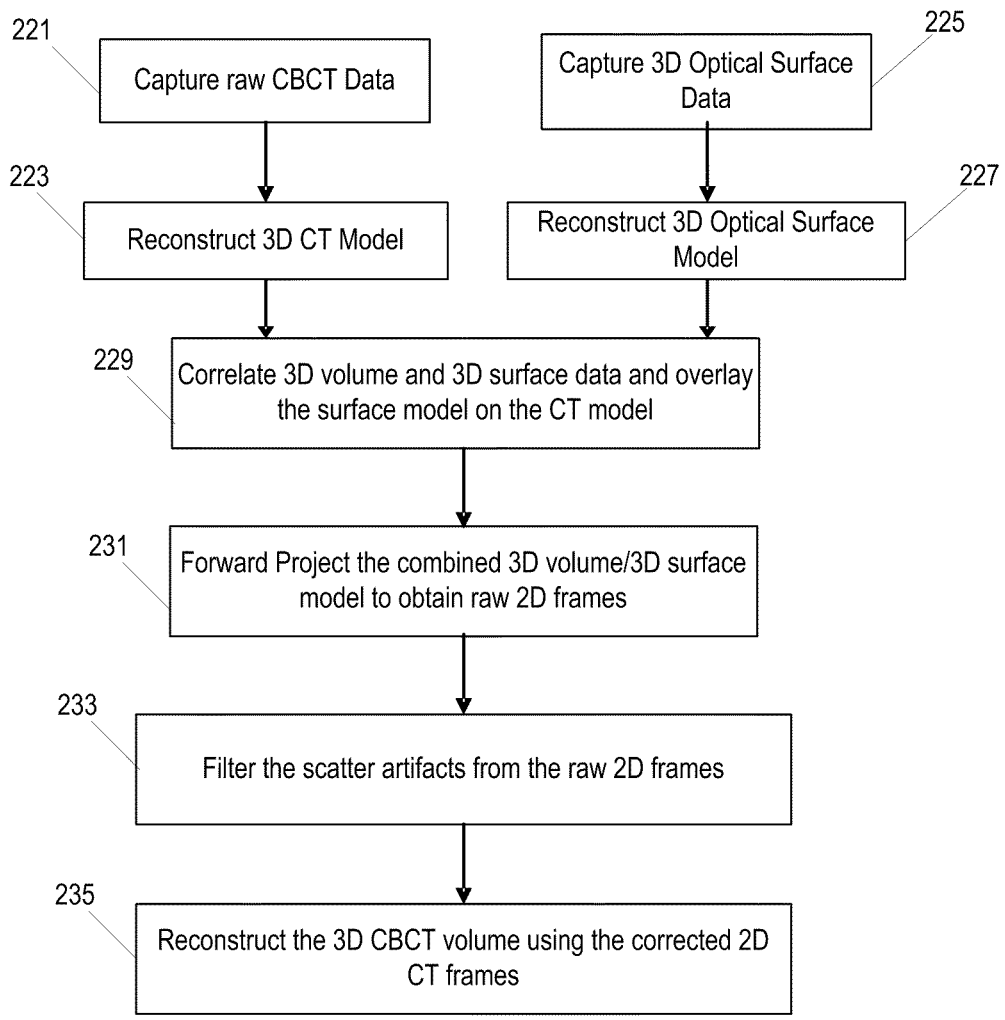
FIG. 3 is a flowchart showing a second method of using the system of FIG. 1A to remove artifacts from a CT model.

An alternative approach for combining the CT and optically derived surface data as presented in FIG. 3. As in the method of FIG. 2 above, the CT and optical data are both captured (steps 221, 225) and are both processed to produce 3D volumetric data (steps 223, 227). The data models are again correlated and overlaid (step 229). Once correlated, the two volumetric datasets in the combined data set are then both forward-projected in order to create a set of two-dimensional projection images (step 231). Optically-derived data is then used to identify the teeth surface and filter or compensate for the artifact-causing elements (created by scatter and beam hardening associated with metal in the image volume) in the images or frames that lead to artifacts in the reconstructed images (step 233). The filtering process removes artifacts before a three-dimensional model is reconstructed from the two-dimensional projection images (step 235).

Figure 4:
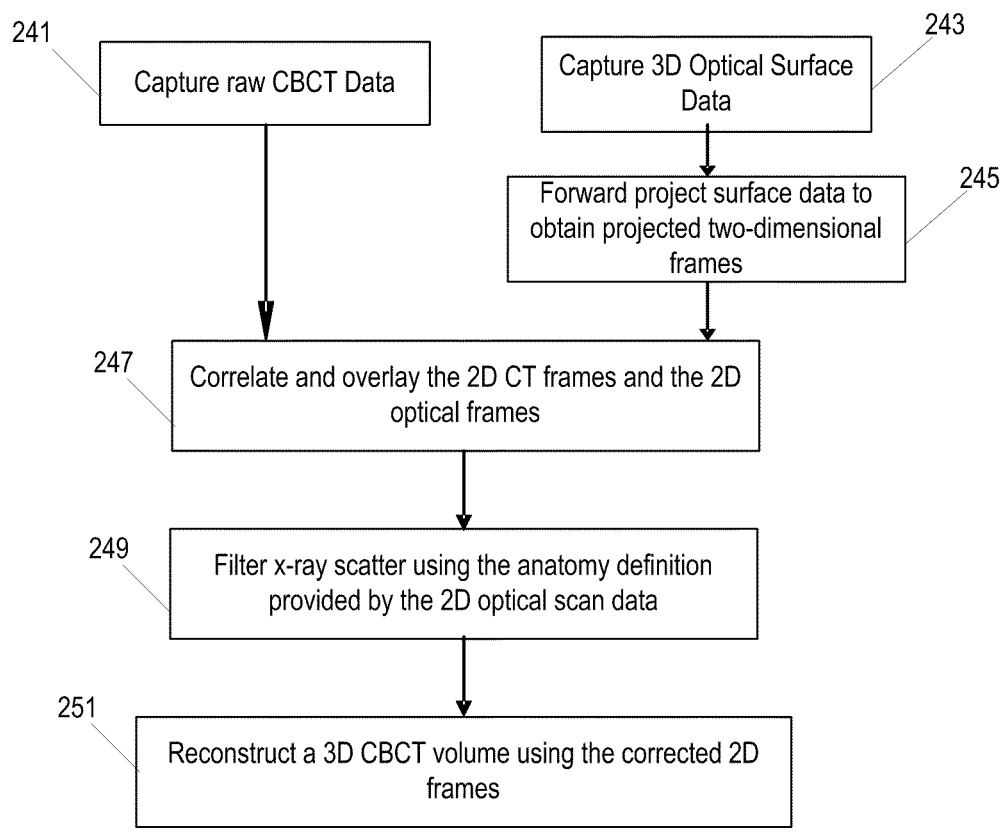
FIG. 4 is a flowchart showing a third method of using the system of FIG. 1A to remove artifacts from a CT model.

A third approach to combining the CT and optically-derived surface data is presented in FIG. 4. In this case, the CT and optical data are both captured as described above (steps 241, 243). However, instead of generating two three-dimensional models, the optical surface data is forward projected to generate two-dimensional projection images (step 245). The two dimensional images from the CT data and the two-dimensional projection images are correlated and overlaid (step 247). Artifact-causing elements that lead to artifacts in the reconstructed images are filtered from the raw CT data using the anatomy defined by the two-dimensional optical frames (step 249). A three-dimensional CT model is then constructed from the filtered and corrected CT data frames.

Thus, the invention provides, among other things, a system for capturing CT data, generating a CT model, and removing artifacts from the generated CT model by capturing surface scan data of the patient's teeth, overlaying the surface scan data onto the CT model, and identifying, reducing, and removing artifacts that are outside of the surface scan data. Various features and advantages are set forth in the following claims.

What is claimed is:

1. A system for removing artifacts caused by x-ray reflective materials from an x-ray image of a patient's teeth, the system comprising:
   an x-ray source;
   an x-ray detector that captures x-ray images;
   a surface scanner that captures a surface scan of the patient's teeth; and
   an image processor that constructs a three-dimensional CT model of the patient's teeth from the x-ray images and a three-dimensional surface model of the patient's teeth from the surface scan,
   the image processor resizing and orienting at least one of the surface model and the CT model so that the surface model and the CT model are of a same scale and orientation,
   overlaying the surface model on the CT model,
   detecting data points in the combined data set that extend beyond a surface of the patient's teeth in the surface model, wherein the detected data points represent artifacts in the CT model,
   removing the detected data points from the CT model by interpolation of the detected data points to create an artifact-reduced CT model, and
   displaying the artifact-reduced CT model.

2. The system of claim 1, wherein the surface scanner includes a laser scanning system.

3. The system of claim 1, wherein the surface scanner includes a structured light scanning system.

4. The system of claim 1, wherein the image processor determines that all data points in the combined data set that extend beyond the surface of the patient's teeth in the surface model are artifacts, and removes the artifacts from the CT model.

5. The system of claim 1, wherein the image processor compares a value of data points in the combined data set that extend beyond the surface of the patient's teeth in the surface model to a threshold, determines whether the detected data points are artifacts based on the comparison, and removes the artifacts from the CT model.

6. The system of claim 1, wherein the image processor performs a filtering operation on the data points in the combined data set that extend beyond the surface of the patient's teeth in the surface model, determines whether the detected data points are artifacts based on the filtering operation, and removes the artifacts from the CT model.

7. The system of claim 1, wherein the image processor generates a first two-dimensional data slice from the surface model corresponding to a first two-dimensional data slice from the CT model, and detects data points in the combined data set that extend beyond a surface of the patient's teeth in the surface model by comparing the first two-dimensional data slice from the surface model to the first two-dimensional data slice from the CT model.

8. The system of claim 7, wherein the first two-dimensional data slice from the surface model includes surface data for a first tooth.

9. The system of claim 8, wherein the image processor generates a second two-dimensional data slice from the surface model including surface data for a second tooth and corresponding to a second two-dimensional data slice from the CT model after removing artifacts associated with the first tooth.

10. The system of claim 7, wherein the first two-dimensional data slice from the surface model includes surface data for a plurality of teeth.

11. The system of claim 10, wherein the image processor generates a second two-dimensional data slice from the surface model including data for the same plurality of teeth at a location parallel to the first two-dimensional data slice from the surface model and corresponding to a second two-dimensional data slice from the CT model after removing the artifacts associated with the first two-dimensional data slice from the CT model.

12. The system of claim 7, wherein the first two-dimensional data slice from the surface model includes surface data for all of the patient's teeth.

\* \* \* \* \*